(12) United States Patent
Shulze et al.

(10) Patent No.: US 8,715,341 B2
(45) Date of Patent: *May 6, 2014

(54) DRUG-DELIVERY ENDOVASCULAR STENT AND METHOD OF FORMING THE SAME

(71) Applicants: John E. Shulze, Rancho Santa Margarita, CA (US); Ronald E. Betts, La Jolla, CA (US); Douglas R. Savage, Del Mar, CA (US)

(72) Inventors: John E. Shulze, Rancho Santa Margarita, CA (US); Ronald E. Betts, La Jolla, CA (US); Douglas R. Savage, Del Mar, CA (US)

(73) Assignee: Biosensors International Group, Ltd., Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 13/647,977

(22) Filed: Oct. 9, 2012

(65) Prior Publication Data

US 2013/0035754 A1 Feb. 7, 2013

Related U.S. Application Data

(60) Continuation of application No. 12/696,318, filed on Jan. 29, 2010, now Pat. No. 8,308,795, which is a division of application No. 10/946,275, filed on Sep. 20, 2004, now Pat. No. 7,727,275, which is a continuation of application No. 10/133,814, filed on Apr. 24, 2002, now Pat. No. 6,939,376.

(51) Int. Cl.
*A61F 2/06* (2013.01)

(52) U.S. Cl.
USPC ........ 623/1.46; 623/1.15; 623/1.42; 623/1.43

(58) Field of Classification Search
USPC .......................... 623/1.1–1.24; 424/423, 426; 427/2.25–2.3, 232, 235, 355
See application file for complete search history.

(56) References Cited

U.S. PATENT DOCUMENTS 3,929,992 A    12/1975  Sehgal et al.
4,316,885 A    2/1982   Rakhit
(Continued)

FOREIGN PATENT DOCUMENTS

EP    0551182    7/1993
EP    0470246    6/1995
(Continued)

OTHER PUBLICATIONS

Denny W.A. and Cain, B.F., "Potential antitumor agents. 27. Quantitative structure—antileukemic (L1210) activity relationships for the omega-[4-(9-acridinylamino)phenyl]alkanoic acids," 1978, *Journal of Medicinal Chemistry*, 21(5); 430-437.

(Continued)

*Primary Examiner* — David Isabella
*Assistant Examiner* — Yashita Sharma
(74) *Attorney, Agent, or Firm* — Kilpatrick Townsend & Stockton LLP

(57) ABSTRACT

An intravascular stent and method for inhibiting restenosis, following vascular injury, is disclosed. The stent has an expandable, linked-filament body and a drug-release coating formed on the stent-body filaments, for contacting the vessel injury site when the stent is placed in-situ in an expanded condition. The coating releases, for a period of at least 4 weeks, a restenosis-inhibiting amount of a monocyclic triene immunosuppressive compound having an alkyl group substituent at carbon position 40 in the compound. The stent, when used to treat a vascular injury, gives good protection against clinical restenosis, even when the extent of vascular injury involves vessel overstretching by more than 30% diameter. Also disclosed is a stent having a drug-release coating composed of (i) 10 and 60 weight percent poly-dl-lactide polymer substrate and (ii) 40-90 weight percent of an anti-restenosis compound, and a polymer undercoat having a thickness of between 1-5 microns.

17 Claims, 9 Drawing Sheets

(56) References Cited

U.S. PATENT DOCUMENTS

| | | | |
|---|---|---|---|
| 4,650,803 A | 3/1987 | Stella et al. |
| 4,885,171 A | 12/1989 | Surendra et al. |
| 4,990,155 A | 2/1991 | Wilkoff |
| 5,100,899 A | 3/1992 | Caine |
| 5,120,842 A | 6/1992 | Failli et al. |
| 5,151,413 A | 9/1992 | Caufield et al. |
| 5,252,579 A | 10/1993 | Skotnicki et al. |
| 5,258,389 A | 11/1993 | Goulet et al. |
| 5,288,711 A | 2/1994 | Mitchell et al. |
| 5,306,286 A | 4/1994 | Stack et al. |
| 5,342,348 A | 8/1994 | Kaplan |
| 5,362,718 A | 11/1994 | Skotnicki et al. |
| 5,443,458 A | 8/1995 | Eury |
| 5,447,724 A | 9/1995 | Helmus et al. |
| 5,464,650 A | 11/1995 | Berg et al. |
| 5,516,781 A | 5/1996 | Morris et al. |
| 5,527,337 A | 6/1996 | Stack et al. |
| 5,545,208 A | 8/1996 | Wolff et al. |
| 5,607,467 A | 3/1997 | Froix |
| 5,609,629 A | 3/1997 | Fearnot et al. |
| 5,649,977 A | 7/1997 | Campbell |
| 5,665,772 A | 9/1997 | Cottens et al. |
| 5,707,385 A | 1/1998 | Williams et al. |
| 5,733,327 A | 3/1998 | Igaki et al. |
| 5,776,184 A | 7/1998 | Tuch |
| 5,824,048 A | 10/1998 | Tuch |
| 5,824,049 A | 10/1998 | Ragheb et al. |
| 5,837,313 A | 11/1998 | Ding et al. |
| 5,860,999 A | 1/1999 | Schnepp-Pesch et al. |
| 5,869,127 A | 2/1999 | Zhong |
| 5,873,904 A | 2/1999 | Ragheb et al. |
| 5,902,317 A | 5/1999 | Kleshinski et al. |
| 5,912,253 A | 6/1999 | Cottens et al. |
| 6,013,853 A | 1/2000 | Athanasiou et al. |
| 6,042,606 A | 3/2000 | Frantzen |
| 6,042,875 A | 3/2000 | Ding et al. |
| 6,080,177 A | 6/2000 | Igaki et al. |
| 6,099,562 A | 8/2000 | Ding et al. |
| 6,120,536 A | 9/2000 | Ding et al. |
| 6,129,755 A | 10/2000 | Mathis et al. |
| 6,153,252 A | 11/2000 | Hossainy et al. |
| 6,174,329 B1 | 1/2001 | Callol et al. |
| 6,179,817 B1 | 1/2001 | Zhong |
| 6,190,406 B1 | 2/2001 | Duering et al. |
| 6,197,781 B1 | 3/2001 | Guitard et al. |
| 6,214,901 B1 | 4/2001 | Chudzik et al. |
| 6,231,600 B1 | 5/2001 | Zhong |
| 6,239,124 B1 | 5/2001 | Zenke et al. |
| 6,273,913 B1 | 8/2001 | Wright et al. |
| 6,277,983 B1 | 8/2001 | Shaw |
| 6,299,604 B1 | 10/2001 | Ragheb et al. |
| 6,368,658 B1 | 4/2002 | Schwartz et al. |
| 6,384,046 B1 | 5/2002 | Schuler et al. |
| 6,585,764 B2 | 7/2003 | Wright et al. |
| 6,607,598 B2 | 8/2003 | Schwarz et al. |
| 6,641,611 B2 | 11/2003 | Jayaraman |
| 6,663,881 B2 | 12/2003 | Kunz et al. |
| 6,670,398 B2 | 12/2003 | Edwards et al. |
| 6,743,463 B2 | 6/2004 | Weber et al. |
| 6,746,773 B2 | 6/2004 | Llanos et al. |
| 6,790,228 B2 | 9/2004 | Hossainy et al. |
| 6,863,685 B2 | 3/2005 | Davila et al. |
| 6,908,622 B2 | 6/2005 | Barry et al. |
| 6,939,376 B2 | 9/2005 | Shulze et al. |
| 7,179,283 B2 | 2/2007 | DiMatteo et al. |
| 7,294,145 B2 | 11/2007 | Ward |
| 2001/0027340 A1 | 10/2001 | Wright et al. |
| 2001/0029351 A1 | 10/2001 | Falotico et al. |
| 2002/0038146 A1 | 3/2002 | Harry |
| 2002/0051730 A1 | 5/2002 | Bodnar et al. |
| 2002/0082679 A1 | 6/2002 | Sirhan et al. |
| 2002/0111590 A1 | 8/2002 | Davila et al. |
| 2002/0156022 A1 | 10/2002 | Edwards et al. |
| 2003/0033007 A1 | 2/2003 | Sirhan et al. |
| 2003/0050692 A1 | 3/2003 | Sirhan et al. |
| 2003/0059454 A1 | 3/2003 | Barry et al. |
| 2003/0068355 A1 | 4/2003 | Shanley et al. |
| 2003/0077310 A1 | 4/2003 | Pathak et al. |
| 2003/0083646 A1 | 5/2003 | Sirhan et al. |
| 2003/0143315 A1 | 7/2003 | Pui et al. |
| 2003/0225450 A1 | 12/2003 | Shulze et al. |
| 2004/0010002 A1 | 1/2004 | Wasik et al. |
| 2004/0024450 A1 | 2/2004 | Shulze et al. |
| 2004/0030380 A1 | 2/2004 | Shulze et al. |
| 2005/0038505 A1 | 2/2005 | Shulze et al. |
| 2006/0193892 A1* | 8/2006 | Furst et al. ............ 424/426 |
| 2006/0229706 A1 | 10/2006 | Shulze et al. |

FOREIGN PATENT DOCUMENTS

| | | |
|---|---|---|
| EP | 0867438 | 9/1998 |
| EP | 0950386 | 10/1999 |
| EP | 0970711 | 1/2000 |
| EP | 1192957 | 4/2002 |
| JP | 10192413 | 7/1998 |
| WO | WO 95/16691 | 6/1995 |
| WO | WO 97/35575 | 10/1997 |
| WO | WO 97/37617 | 10/1997 |
| WO | WO 98/36784 | 8/1998 |
| WO | WO 99/07308 | 2/1999 |
| WO | WO 00/32255 | 6/2000 |
| WO | WO 01/14387 | 3/2001 |
| WO | WO 01/45763 | 6/2001 |
| WO | WO 01/66161 | 9/2001 |
| WO | WO 01/87368 | 11/2001 |
| WO | WO 02/26162 | 4/2002 |
| WO | WO 02/26281 | 4/2002 |
| WO | WO 02/32347 | 4/2002 |

OTHER PUBLICATIONS

Ichihashi, T., et al., "A quantitative concept of the mechanism of intestinal lymphatic transfer of lipophilic molecules," 1994, *Pharmaceutical Research*, 11(4); 508-512.

Marx, S. et al., "Bench to Bedside: The Development of Rapamycin and Its Application to Stent Restenosis," 2001, *Circulation*, 104, pp. 852-855.

Nishimura, T. et al., "40-*O*-(2-Hydroxyethyl)-rapamycin Attenuates Pulmonary Arterial Hypertension and Neointimal Formation in Rats," 2001, *Am. J. Respir. Crit. Care Med*, 163(2): 498-502.

Schwartz et al., "Restenosis after balloon angioplasty. A practical proliferative model in porcine coronary arteries," 1990, *Circulation*, 82(6): 2190-2200.

Sousa et al., "Lack of Neointimal Proliferation After Implantation of Sirolimus-Coated Stents in Human Coronary Arteries : A Quantitative Coronary Angiography and Three-Dimensional Intravascular Ultrasound Study," 2001, *Circulation*, 103(2): 192-195.

European Search Report dated Apr. 5, 2011, issued in related European Patent Application No. 10185483.4.

Japanese Office Action dated Nov. 8, 2011 issued in related Japanese Application No. 2008-209129.

European Office Action Dated Sep. 5, 2012, issued in European Patent Application No. 11185222.4.

\* cited by examiner

DRUG-DELIVERY ENDOVASCULAR STENT AND METHOD OF FORMING THE SAME

CROSS-REFERENCE TO RELATED APPLICTIONS

This application is a continuation Application of U.S. application Ser. No. 12/696,318, filed Jan. 29, 2010, which is a Division of U.S. application Ser. No. 10/946,275, filed Sep. 20, 2004, which is a continuation of U.S. application Ser. No. 10/133,814, filed Apr. 24, 2002, which are incorporated in their entirety herein for all purposes.

FIELD OF THE INVENTION

The present invention relates to an endovascular drug-delivery stent and to a method for treating restenosis.

BACKGROUND OF THE INVENTION

A stent is a type of endovascular implant, usually generally tubular in shape, typically having a lattice, connected-wire tubular construction which is expandable to be permanently inserted into a blood vessel to provide mechanical support to the vessel and to maintain or re-establish a flow channel during or following angioplasty. The support structure of the stent is designed to prevent early collapse of a vessel that has been weakened and damaged by angioplasty. Insertion of stents has been shown to prevent negative remodeling and spasm of the vessel while healing of the damaged vessel wall proceeds over a period of months.

During the healing process, inflammation caused by angioplasty and stent implant injury often causes smooth muscle cell proliferation and regrowth inside the stent, thus partially closing the flow channel, and thereby reducing or eliminating the beneficial effect of the angioplasty/stenting procedure. This process is called restenosis. Blood clots may also form inside of the newly implanted stent due to the thrombotic nature of the stent surfaces, even when biocompatible materials are used to form the stent. While large blood clots may not form during the angioplasty procedure itself or immediately post-procedure due to the current practice of injecting powerful anti-platelet drugs into the blood circulation, some thrombosis is always present, at least on a microscopic level on stent surfaces, and it is thought to play a significant role in the early stages of restenosis by establishing a biocompatible matrix on the surfaces of the stent whereupon smooth muscle cells may subsequently attach and multiply.

Stent coatings are known which contain bioactive agents that are designed to reduce or eliminate thrombosis or restenosis. Such bioactive agents may be dispersed or dissolved in either a bio-durable or bio-erodable polymer matrix that is attached to the surface of the stent wires prior to implant. After implantation, the bioactive agent diffuses out of the polymer matrix and preferably into the surrounding tissue over a period lasting at least 4 weeks, and in some cases up to 1 year or longer, ideally matching the time course of restenosis, smooth muscle cell proliferation, thrombosis or a combination thereof.

If the polymer is bioerodable, in addition to release of the drug through the process of diffusion, the bioactive agent may also be released as the polymer degrades or dissolves, making the agent more readily available to the surrounding tissue environment. Bioerodable stents and biodurable stents are known where the outer surfaces or even the entire bulk of polymer material is porous. For example, PCT Publication No. WO 99/07308, which is commonly owned with the present application, discloses such stents, and is expressly incorporated by reference herein. When bioerodable polymers are used as drug delivery coatings, porosity is variously claimed to aid tissue ingrowth, make the erosion of the polymer more predictable, or to regulate or enhance the rate of drug release, as, for example, disclosed in U.S. Pat. Nos. 6,099,562, 5,873,904, 5,342,348, 5,873,904, 5,707,385, 5,824,048, 5,527,337, 5,306,286, and 6,013,853.

Heparin, as well as other anti-platelet or anti-thrombolytic surface coatings, are known which are chemically bound to the surface of the stent to reduce thrombosis. A heparinized surface is known to interfere with the blood-clotting cascade in humans, preventing attachment of platelets (a precursor to thrombin) on the stent surface. Stents have been described which include both a heparin surface and an active agent stored inside of a coating (see U.S. Patents Nos. 6,231,600 and 5,288,711, for example).

A variety of agents specifically claimed to inhibit smooth muscle-cell proliferation, and thus inhibit restenosis, have been proposed for release from endovascular stents. As examples, U.S. Pat. No. 6,159,488 describes the use of a quinazolinone derivative; U.S. Pat. No. 6,171,609, the use of taxol, and U.S. Pat. No. 5,176,98, the use of paclitaxel, a cytotoxic agent thought to be the active ingredient in the agent taxol. The metal silver is cited in U.S. Pat. No. 5,873,904. Tranilast, a membrane stabilizing agent thought to have anti-inflammatory properties is disclosed in U.S. Pat. No. 5,733,327.

More recently, rapamycin, an immunosuppressant reported to suppress both smooth muscle cell and endothelial cell growth, has been shown to have improved effectiveness against restenosis, when delivered from a polymer coating on a stent. See, for example, U.S. Pat. Nos. 5,288,711 and 6,153,252. Also, in PCT Publication No. WO 97/35575, the monocyclic triene immunosuppressive compound everolimus and related compounds have been proposed for treating restenosis, via systemic delivery.

Ideally, a compound selected for inhibiting restenosis, by drug release from a stent, should have three properties. First, because the stent should have a low profile, meaning a thin polymer matrix, the compound should be sufficiently active to produce a continuous therapeutic dose for a minimum period of 4-8 weeks when released from a thin polymer coating. Secondly, the compound should be effective, at a low dose, in inhibiting smooth muscle cell proliferation.

Finally, endothelial cells which line the inside surface of the vessel lumen are normally damaged by the process of angioplasty and/or stenting. The compound should allow for regrowth of endothelial cells inside the vessel lumen, to provide a return to vessel homeostasis and to promote normal and critical interactions between the vessel walls and blood flowing through the vessel.

SUMMARY OF THE INVENTION

The invention includes, in one aspect, an endovascular stent for placement at a vascular injury site, for inhibiting restenosis at the site. The stent is constructed of a structural member or body formed of one or more filaments and carried on the stent-body filament(s), a bioerodable drug-release coating having a thickness of between 3-15 microns, and composed of (i) 20 and 60 weight percent poly-dl-lactide polymer substrate and (ii) 40-80 weight percent of an anti-restenosis compound. A polymer undercoat having a thickness of between 1-5 microns and disposed between the stent-body filaments and the coating helps to stabilize the coating on the stent filaments. The stent is expandable from a contracted condition in which the stent can be delivered to a vascular injury site via catheter, and an expanded condition in which the stent coating can be placed in contact with the vessel at the injury site. The stent coating is effective to release a restenosis-inhibiting amount of the compound over a period of at least 4 weeks after the stent is placed at the vascular injury site.

In various exemplary embodiments, the anti-restenosis compound is a monocyclic triene immunosuppressive compound, the stent body is a metal-filament structure, the undercoat is formed of a parylene polymer and has a thickness between 0.5 and 5 microns, and the coating has a thickness between 2 and 10 microns. The compound may be present in the coating in an amount between 50% and 75% by weight.

Exemplary macrocyclic triene immunosuppressive compounds have the general form

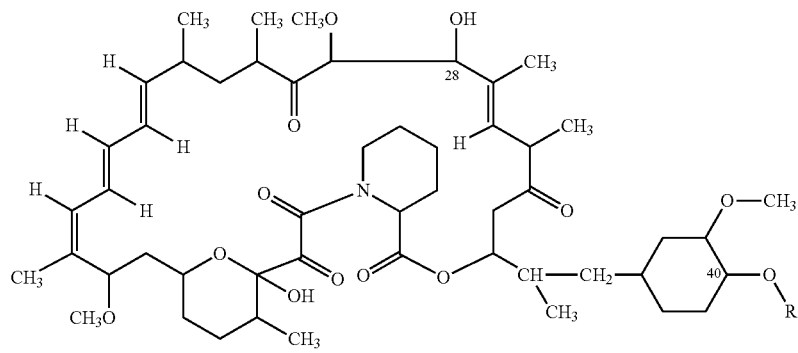

where (i) R is H or $CH_2$—X—OH, and X is a linear or branched alkyl group containing 1 to 7 carbon atoms, when R' is H (R' replaces H at the 28 position O) or (ii) at least one of R and R' have the form

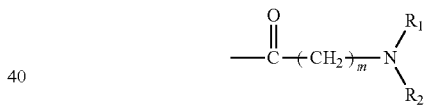

where m is an integer from 1 to 3 and $R_1$ and $R_2$ are each a hydrogen, or an alkyl radical having from one to three carbon atoms, or, alternatively, wherein $R_1$ and $R_2$ together with a nitrogen atom to which they are attached form a saturated heterocyclic ring having four carbon atoms. In an exemplary compound, known as everolimus, R' is H and X is —$CH_2$.

The above stent is employed in a method for inhibiting restenosis in a vascular injury site, in accordance with another aspect of the invention. In the method, the stent is delivered to a vascular injury site, and expanded to bring the stent coating in contact with the vessel at the injury site. The coating is effective to release a restenosis-inhibiting amount of the compound over a period of at least 4 weeks.

In another aspect, the invention includes an endovascular stent for placement at a vascular injury site for inhibiting restenosis at the site. The stent is composed of a structural member or body formed of one or more filaments and carried on the stent-body filament(s), a drug-release coating having a thickness of between 3-25 microns, and composed of between (i) 20 and 70 weight percent polymer substrate and (ii) 30-80 weight percent macrocyclic triene immunosuppressive compound having the form:

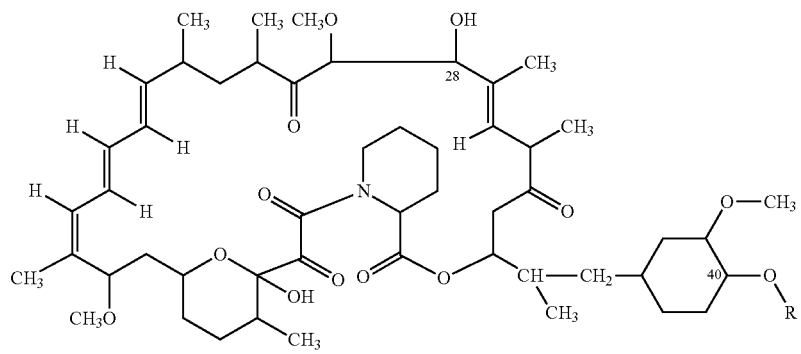

where R is CH$_2$—X—OH, and X is a linear group containing 1 to 7 carbon atoms.

The stent is expandable from a contracted condition in which the stent can be delivered to a vascular injury site via catheter, and an expanded condition in which the stent coating can be placed in contact with the vessel at the injury site. The coating is effective to release the restenosis-inhibiting amount of the compound over a period of at least 4 weeks after the stent is placed at the vascular injury site.

In various exemplary embodiments, R is CH$_2$—X—OH where X is —CH$_2$—, the stent body is a metal-filament structure, and the polymer substrate in the coating is a polymethylmethacrylate, ethylene vinyl alcohol, or poly-dl-lactide polymer.

In one exemplary embodiment, the polymer substrate in the coating is formed of a bioerodable poly-dl-lactide having a thickness between 3-20 microns and the compound is present in the coating at an initial concentration of between 20 and 70 weight percent of coating. Particularly where the amount of the compound in the coating is greater than about 40 weight percent, the stent may further include a parylene polymer undercoat having a thickness of between 1-5 microns, disposed between the filaments of the stent body and the poly-dl-lactide coating substrate.

Alternatively, both the stent body and coating substrate may be formed of a bioerodable polymer, such poly-l-or poly-dl-lactide forming the stent-body filaments, and poly-dl-lactide forming the coating substrate.

The stent coating may be constructed to contact blood flowing through the stent when the stent is placed at the site in its expanded condition. In this embodiment, the coating may further contain a bioactive agent such as an anti-platelet, fibrinolytic, or thrombolytic agent in soluble crystalline form. Exemplary anti-platelet, fibrinolytic, or thrombolytic agents are heparin, aspirin, hirudin, ticlopidine, eptifibatide, urokinase, streptokinase, tissue plasminogen activator (TPA), or mixtures thereof.

In still another aspect, the invention provides an improvement in a method for restenosis at a vascular injury site, by placing at the site an endovascular stent designed to release a macrocyclic triene immunosuppressive compound over an extended period. The improvement includes employing as the macrocyclic triene immunosuppressive compound, a compound having the formula:

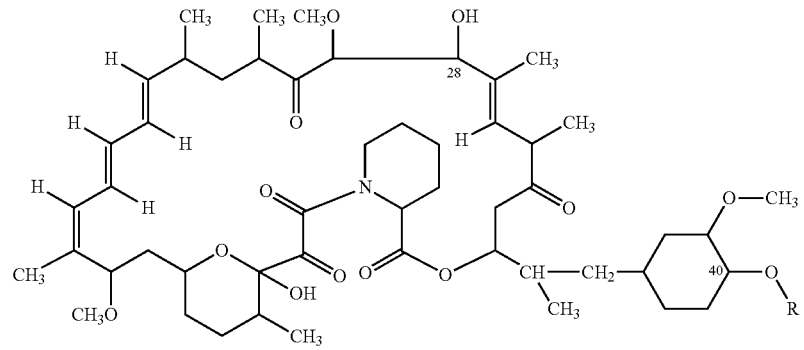

where R is CH$_2$—X—OH, and X is a linear alkyl group containing 1 to 7 carbon atoms. In one exemplary compound, X is —CH$_2$—.

Various exemplary embodiments of the stent composition are given above. Also disclosed is a novel method for coating the filaments of a stent body with a drug-containing polymer coating. The method employs an automated controller to regulate the flow of a polymer or polymer-drug solution onto the filaments of a stent body, to achieve one of a variety of stent-coating features, including a uniform thickness coating on one or more sides of the stent-body filaments, greater coating thickness on the outer (or inner) surfaces of the stent body than on the other side, inner and outer coatings containing different drugs, and/or coating thickness gradients or discrete coating patches on the stent body.

These and other objects and features of the invention will become more fully apparent when the following detailed description of the invention is read in conjunction with the accompanying drawings.

DETAILED DESCRIPTION OF THE INVENTION

I. Endovascular stent

Figure 1:
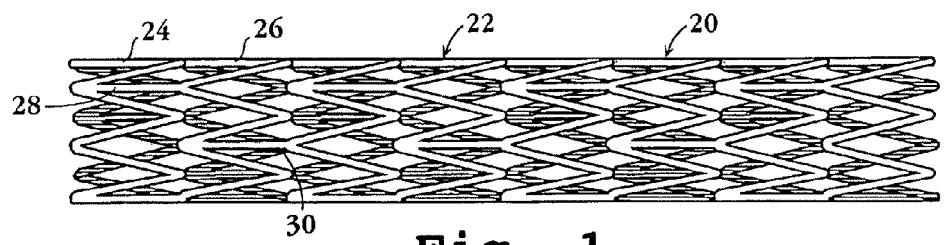
FIGS. 1 and 2 illustrate an endovascular stent having a metal-filament body, and formed in accordance with one embodiment of the present invention, showing the stent in its contracted (FIG. 1) and expanded (FIG. 2) conditions.
Figure 2:
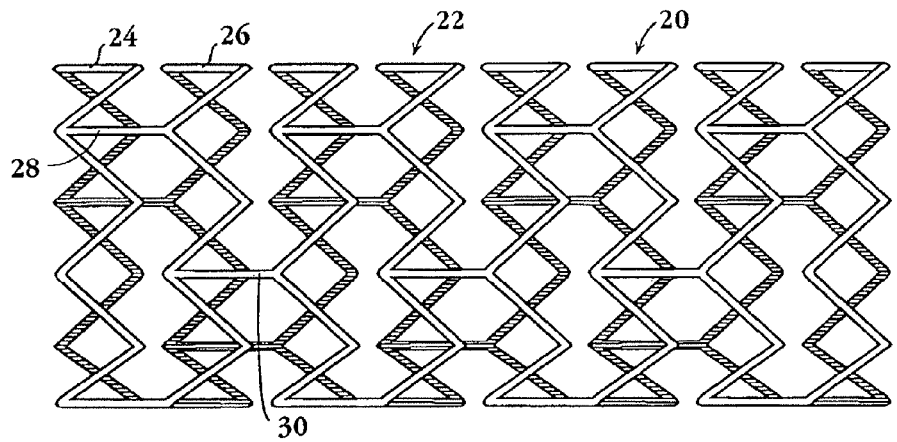

FIGS. 1 and 2 show a stent 20 constructed in accordance with the invention, in the stent's contracted and expanded states, respectively. The stent includes a structural member or body 22 and an outer coating for holding and releasing an anti-restenosis compound, as will be described further below with reference to FIGS. 3 and 4.

A. Stent body In the embodiment shown, the stent body is formed of a plurality of linked tubular members by filaments, such as members 24, 26. Each member is has an expandable zig-zag, sawtooth, or sinusoidal wave structure. The members are linked by axial links, such as links 28, 30 joining the peaks and troughs of adjacent members. As can be appreciated, this construction allows the stent to be expanded from a contracted condition, shown in FIG. 1, to an expanded condition, shown in FIG. 2, with little or no change in the length of the stent. At the same time, the relatively infrequent links between peaks and troughs of adjacent tubular members allows the stent to accommodate bending. This feature may be particularly important when the stent is being delivered to a vascular site in its contracted state, in or on a catheter. The stent has a typical contracted-state diameter (FIG. 1) of between 0.5-2 mm, more preferably 0.71 to 1.65 mm, and a length of between 5-100 mm. In its expanded state, shown in FIG. 2, the stent diameter is at least twice and up to 8-9 times that of the stent in its contracted state. Thus, a stent with a contracted diameter of between 0.7 to 1.5 mm may expand radially to a selected expanded state of between 2-8 mm or more.

Stents having this general stent-body architecture of linked, expandable tubular members are known, for example, as described in PCT Publication No. WO 99/07308, which is commonly owned with the present application, and which is expressly incorporated by reference herein. Further examples are described in U.S. Pat. Nos. 6,190,406, 6,042,606, 5,860, 999, 6,129,755, or 5,902,317, which patents are incorporated by reference herein. Alternatively, the structural member in the stent may have a continuous helical ribbon construction, that is, where the stent body is formed of a single continuous ribbon-like coil. The basic requirement of the stent body is that it be expandable, upon deployment at a vascular injury site, and that it is suitable for receiving a drug-containing coating on its outer surface, for delivering drug contained in the coating into the vessel wall (i.e. medial, adventitial, and endothelial layers of tissue) lining the vascular target site. Preferably, the body also has a lattice or open structure, allowing endothelial cell wall ingrowth "through" the stent from outside to inside.

B. Stent coatings

According to an important feature of the invention, the stent filaments are coated with a drug-release coating composed of a polymer matrix and an anti-restenosis compound (active compound) distributed within the matrix for release from the stent over an at least a several week period, typically 4-8 weeks, and optionally over a 2-3-month period or more.

Figure 3:
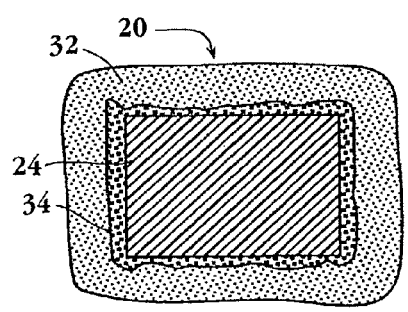
FIG. 3 is an enlarged cross-sectional view of a coated metal filament in the stent of FIG. 1.

FIG. 3 shows, in enlarged sectional view, a stent filament 24 having a coating 32 that covers the filament completely on all sides, that is, on top (the filament side forming the outer surface of the stent body) bottom (the filament side forming the interior surface of the stent) and the opposing filament sides. As will be discussed further below, the coating has a thickness typically between 3 and 30 microns, depending on the nature of the polymer matrix material forming the coating and the relative amounts of polymer matrix and active compound. Ideally, the coating is made as thin as possible, e.g., 15 microns or less, to minimize the stent profile in the vessel at the injury site.

The coating should also be relatively uniform in thickness across the upper (outer) surfaces, to promote even distribution of released drug at the target site. Methods for producing a relatively even coating thickness on stent filaments are discussed below in Section II.

Also shown in FIG. 3 is a polymer underlayer 34 disposed between the stent filament and the coating. The purpose of the underlayer is to help bond the coating to the stent-body filaments, that is, to help stabilize the coating on the filaments. As will be seen below, this function is particularly valuable where the coating is formed of a polymer substrate containing a high percentage of anti-restenosis compound, e.g. between 35-80 weight percent compound. One exemplary underlayer polymer is parylene used in conjunction with a polymer substrate formed of bioerodable (poly-dl-lactide). Other suitable polymer underlayers are ethylene vinyl alcohol (EVOH), paryLAST™, silicone, TEFLON™ and other fluoropolymers, that may be deposited on the metal stent surfaces by plasma-coating or other coating or deposition processes. The underlayer has a typical thickness between 1-5 microns.

The polymer forming the substrate may be any biocompatible polymer material from which entrapped compound can be released by diffusion and/or released by erosion of the polymer matrix. Two well-known non-erodable polymers for the coating substrate are polymethylmethacrylate and ethylene vinyl alcohol. Methods for preparing these polymers in a form suitable for application to a stent body are described for example, in US 2001/0027340A1 and WO00145763A1, incorporated herein by reference. In general, the limit of drug addition to the polymers is about in the range of 20-40 weight percent.

Bioerodable polymers, particularly poly-dl-lactide polymer, are also suitable for coating substrate material. In one general embodiment, of the invention, the coating is a bioerodable poly-dl-lactide polymer substrate, i.e., poly-dl-lactic acid polymer, that may contain up to 80% by dry weight of the active compound distributed within the polymer substrate. More generally, the coating contains 35-80% dry weight active compound and 20-65% percent by dry weight of the polymer. Exemplary coatings include 25-50% dry weight polymer matrix and 50-75 weight percent active compound. The polymer is formulated with the active compound for deposition on the stent filaments as detailed in Section II below.

A variety, of anti-restenosis compounds may be employed in the embodiment, including anti-proliferative agents, such as taxol, antisense compounds, doxorubicin, and most particularly, macrocyclic triene immunosuppressive compounds having the general structure indicated below. The latter class of compounds, and their synthesis, are described, for example in U.S. Pat. Nos. 4,650,803, 5,288,711, 5516781, 5665772 and 6,153,252, in PCT Publication No. WO 97/35575, and in published U.S. patent applications Nos. 6273913B1, 60/176086, 20000212/17, and 2001002935/A1, all of which are incorporated herein by reference. Exemplary macrocyclic triene immunosuppressive compounds have the form:

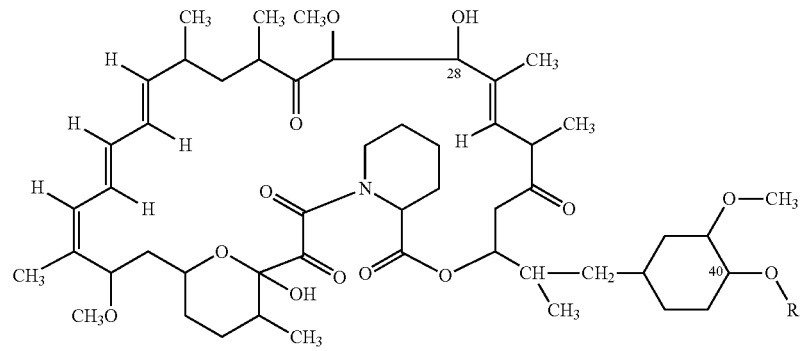

where (i) R is H or $CH_2$—X—OH, and X is H or is a linear or branched alkyl group containing 1 to 7 carbon atoms, when R' is H (R' replaces H at the 28 position O) or (ii) at least one of R and R' have the form

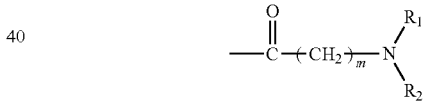

where m is an integer from 1 to 3 and $R_1$ and $R_2$ are each a hydrogen, or an alkyl radical having from one to three carbon atoms, or, alternatively, wherein $R_1$ and $R_2$ together with a nitrogen atom to which they are attached form a saturated heterocyclic ring having four carbon atoms. In an exemplary compound, known as everolimus, R' is H and X is —$CH_2$.

One preferred coating is formed of 25-50 weight percent poly-dl-lactide polymer substrate, and 50-75 weight percent macrocyclic triene immunosuppressant compound, having a coating thickness of between 3-15 microns. The underlayer is formed of parylene, and has a thickness between 1-5 microns. This embodiment typically contains an amount of compound equal to about 15 micrograms drug/mm of stent length.

In another exemplary embodiment, the coating is formed of 15-35 weight percent of an erodable or non-erodable polymer substrate, and 65-85 weight percent of a macrocyclic triene compound. The coating thickness is preferably 10-30 microns, and the stent may include a 1-5 micron polymer underlayer, e.g., parylene underlayer. This embodiment typically contains an amount of compound equal to about 15 micrograms drug/mm of stent length. The active compound has the form

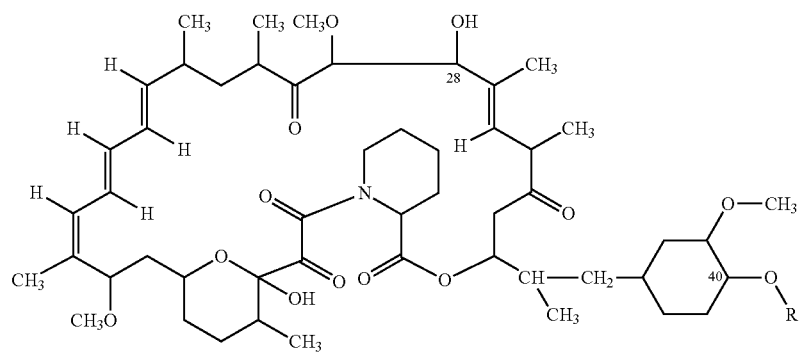

where R is CH$_2$—X—OH, and X is a linear alkyl group containing 1 to 7 carbon atoms. A preferred compound is everolimus, where X=—CH$_2$. Compounds in which X is a 2, 3, 4, 5, 6, or 7 carbon alkyl group, either alone or in any combination, as well as application of acetate esters of the foregoing compounds, including everolimus, are also suitable for the invention.

The coating may additionally include a second bioactive agent effective to minimize blood-related events, such as clotting, that may be stimulated by the original vascular injury, the presence of the stent; or to improve vascular healing at the injury site. Exemplary second agents include anti-platelet, fibrinolytic, or thrombolytic agents in soluble crystalline form. Exemplary anti-platelet, fibrinolytic, or thrombolytic agents are heparin, aspirin, hirudin, ticlopadine (sp), eptifibatide, urokinase, streptokinase, tissue plasminogen activator (TPA), or mixtures thereof. The amount of second-agent included in the stent coating will be determined by the period over which the agent will need to provide therapeutic benefit. Typically, the agent will be beneficial over the first few days after vascular injury and stent implantation, although for some agents, longer period of release of the agent will be required:

The second agent may be included in the coating formulation that is applied to the stent-body filaments, according to known methods.

C. Bioerodable Stent

In another general embodiment, both the stent body and polymer coating are formed of a bioerodable polymer, allowing complete resorption of the stent over time. The stent preferably is an expandable coiled stent having a helical-ribbon filament forming the stent body (not shown). Self-expandable coil stents are described in U.S. Pat. No. 4,990,155 for implantation into blood vessels and are incorporated herein by reference.

A coiled stent, may be formed using a preform with the final expanded diameter of the preform specified to be slightly larger than the internal lumen size of the blood vessel to be treated with the coil (3.5 mm OD±1 mm would be common for a coronary artery). More generally, the stent may be formed by molding, in its expanded shape, and placed in its contracted state by twisting around the stent's long axis or forcing the stent radially into a contracted condition for delivery to the blood vessel when mounted on the tip of a catheter. The stent has a total thickness preferably between about 100 and 1000 microns, and a total length of between 0.4 and 10 cm. In fact, an important advantage of a bioerodable stent of this type is that relatively long stents, e.g., over 3 cm in length, can be readily delivered and deployed at a vascular injury site.

Methods for forming balloon-expandable stents formed of a knitted, bioerodable polymer filament such as poly-l-lactide have been reported (U.S. Pat. No. 6,080,177). A version of the device has also been adapted to release drugs (U.S. Pat. No. 5,733,327).

A preferred polymer material for forming the stent is poly-l-or poly-dl-lactide (U.S. Pat. No. 6,080,177). As indicated above, the stent body and coating may be formed integrally as a single expandable filament stent having anti-restenosis compound contained throughout. Alternatively, a bioerodable coating may be applied to a preformed bioerodable body, as detailed in Section II below. In the latter case, the stent body may be formed of one bioerodable polymer, such as poly-l-lactide polymer, and the coating from a second polymer, such as poly-dl-lactide polymer. The coating, if applied to a preformed stent, may have substantially the same compositional and thickness characteristics described above.

Figure 4:
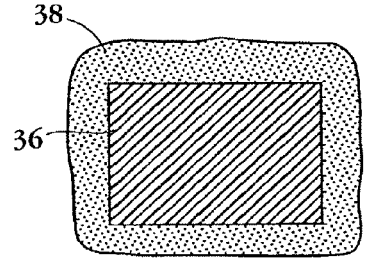
FIG. 4 is an enlarged cross-sectional view of coated erodable polymer stent.

FIG. 4 shows a cross section of a filament, e.g., helical ribbon, in a bioerodable stent of the type just described, having separately formed body and coating. The figures show an internal bioerodable stent filament 36 coated on all sides with a bioerodable coating 38. An exemplary coating is formed of poly-dl-lactide and contains between 20-40 weight percent anti-restenosis drug, such as a macrocyclic triene immunosuppressant compound, and 60-80 weight percent polymer substrate. In another general embodiment, the coating contains 45-75 weight percent compound, and 25-55 weight percent polymer matrix. Other types of anti-restenosis compounds, such as listed above, may be employed in either embodiment.

The bioerodable stent has the unique advantage of treating the entire vessel with one device, either in conjunction with pre-dilitation of the vessel with balloon angioplasty if large obstructions are present, or as a prophylactic implant in patients of high risk of developing significant future blockages. Since the stent is fully biodegradeable, it does not affect the patient's chances for later uncomplicated surgery on the vessel, as a "full metal jacket, " i.e., a string of drug eluting stents containing metal substrates, does.

A secondary agent, such as indicated above, may be incorporated into the coating for release from the coating over a desired time period after implantation. Alternatively, if a secondary agent is used, it may be incorporated into the stent-body filament if the coating applied to the stent body does not cover the interior surfaces of the stent body. The coating methods described below in Section II with respect to a metal-filament stent body are also suitable for use in coating a polymer-filament stent body.

II. Stent coating methods

Figure 5A:
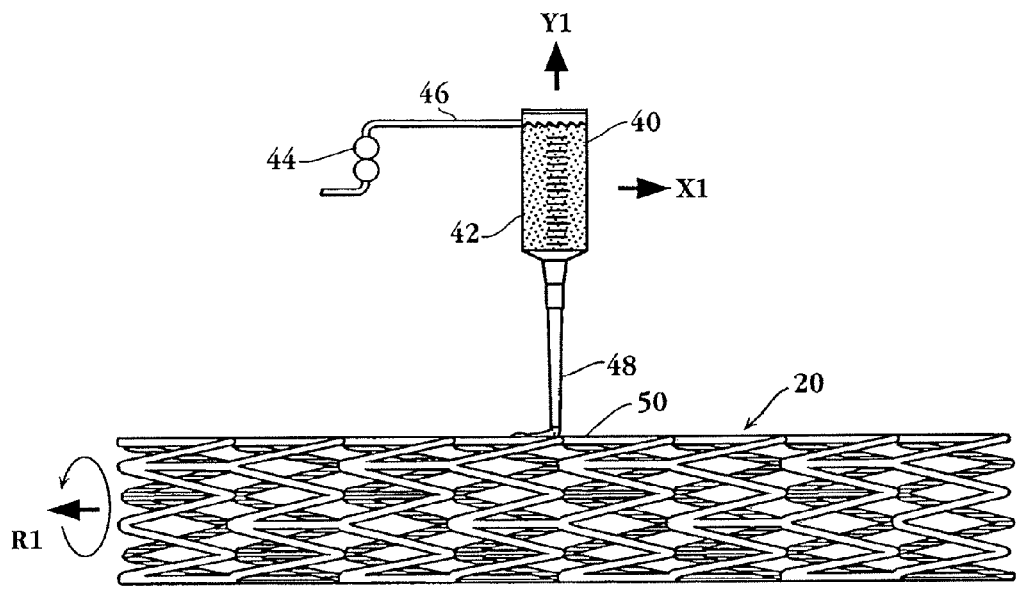
FIGS. 5A and 5B are schematic illustrations of a polymer coating method suitable for use in producing the coated stent of the invention.
Figure 5B:
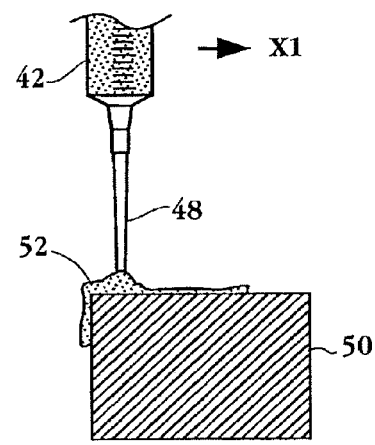

Referring now more particularly to the drawings, FIGS. 5A and 5B are schematic illustrations of the stent coating process according to the invention. A polymer solution 40 is made by dissolving a polymer in a compatible solvent. At least one anti-restenosis compound, and if desired, a secondary agent, is added to the solution, either as a suspension or in solution using the same solvent or a different solvent. The completed mixture is placed in a pressurizable reservoir 42. Connected to the reservoir is a fluid pressurization pump 44.

The pressurization pump may be any source of pressure capable of urging the solvent mixture to move at a programmed rate through a solution delivery tube 46. The pressure pump 44 is under the control of a microcontroller (not shown), as is well known in the field of precision dispensing systems. For example, such a microcontroller may comprise 4-Axis Dispensing Robot Model numbers I&J500-R and I&J750-R available from I&J Fisnar Inc, of Fair Lawn, N.J., which are controllable through an RS-232C communications interface by a personal computer, or precision dispensing systems such as Automove A-400, from Asymtek, of Carlsbad, Calif. A suitable software program for controlling an RS232C interface may comprise the Fluidmove system, also available from Asymtek Inc, Carlsbad, Calif.

Attached to reservoir 42, for example, at the bottom of the reservoir, is a solution delivery tube 48 for delivery of the solvent mixture to the surface of the stent. The pressurizable reservoir 42 and delivery tube 48 are mounted to a moveable support (not shown) which is capable of moving the solvent delivery tube in small steps such as 0.2 mm per step, or continuously, along the longitudinal axis of the stent as is illustrated by arrow X1. The moveable support for pressurizable reservoir 42 and delivery tube 46 is also capable of moving the tip (distal end) of the delivery tube closer to the microfilament surface or up away from the microfilament surface in small steps as shown by arrow Y1.

The uncoated stent is gripped by a rotating chuck contacting the inner surface of the stent at least one end. Axial rotation of the stent can be accomplished in small degree steps, such as 0.5 degree per step, to reposition the uppermost surface of the stent structure for coating by the delivery tube by attachment of a stepper motor to the chuck as is well known in the art. If desirable, the stent can be rotated continuously. The method of precisely positioning a low volume fluid delivery device is well known in the field of X-Y-Z solvent dispensing systems and can be incorporated into the present invention.

The action of the fluid pressurizing pump, X1 and Y1 positioning of the fluid delivery tube, and R1 positioning of the stent are typically coordinated by a digital controller and computer software program, such that the precisely required amount of solution is deposited wherever desired on the surfaces of the stent, whereupon the solvent is allowed to escape, leaving a hardened coating of polymer and agent on the stent surfaces. Typically, the viscosity of the solvent mixture is prepared by varying the amount of solvent, and it ranges from 2 centipoise to 2000 centipoise, and typically can be 300 to 700 centipoise.

Alternatively, the delivery tube can be held at a fixed position and, in addition to the rotation movement, the stent is moved along its longitudinal direction to accomplish the coating process.

The X-Y-Z positioning table and moveable support may be purchased from I&J Fisnar. The solution delivery tube preferred dimensions are preferably between 18-28 gauge stainless steel hypotubes mounted to a suitable locking connector. Such delivery tubes may be obtained from EFD Inc of East Providence, RI. See EFD's selection guide for Special Purpose Tips. The preferred tips are reorder #'s 5118-¼-B through 5121-¼-B "Burr-free passivated stainless steel tips with ¼' length for fast point-to-point dispensing of particle-filled or thick materials", reorder #'s 51150VAL-B "Oval stainless steel tips apply thick pastes, sealants, and epoxies in flat ribbon deposits", and reorder #'s 5121-TLC-B through 5125-TLC-B "Resists clogging of cyanoacrylates and provides additional deposit control for low viscosity fluids. Crimped and Teflon lined". A disposable pressurizable solution reservoir is also available from EFD, stock number 1000Y5148 through 1000Y 5152F. An alternate tip for use with the invention is a glass micro-capillary with an I.D. of about 0.0005 to 0.002 inch, such as about 0.001 inch, which is available from VWR Catalog No 15401-560 "Microhematocrit Tubes", 60 mm length, I.D. 0.5-0.6 mm.

The tubes are further drawn under a Bunsen burner to achieve the desired I.D. for precise application of the polymer/drug/solvent mixture. The programmable microcontroller to operate the stepper motor, and XYZ table is available from Asymtek, Inc. It is within the scope of the invention to use more than one of the fluid dispensing tube types working in concert to form the coating, or alternately to use more than one moveable solution reservoir equipped with different tips, or containing different viscosity solutions or different chemical makeup of the multiple solutions in the same process to form the coating. The chuck and stepper motor system may be purchased from Edmund Scientific of Barrington, N.J.

Typically, as described above, the coating is applied directly onto the outside support surface(s) of the stent, and may or may not cover the entire or a portion(s) of the inside surface(s) of the stent depending on how control is applied to the above described coating system of the present invention, as illustrated in FIGS. 5A and 5B. The latter figure shows application of a coating material 52 to top and side regions of a filament 50. Alternatively, the coating or coating mixture can also be applied directly onto the inside surface of the stent. A thin delivery tip may penetrate through one or more of the cut out areas (i.e. windows) in the wall of the stent structure, and thereby apply the coating mixture directly onto the inside surfaces at desired areas. In this method, it is possible to apply different coating materials having different drug components to outer and inner sides of the filaments. For example, the coating on the outer filament surfaces could contain an anti-restenosis compound, and the coating of the inner filament surfaces, one of the above secondary agents, such an anti-thrombotic or anti-clotting compound. If the stent has a large enough diameter, a thin "L-shaped" delivery tip can be inserted into the stent open ends along the longitudinal axis of the stent for the purpose of applying coating to the inside surfaces.

The polymer for use in the invention includes, but is not limited to, poly(d,l-lactic acid), poly(l-lactic acid), poly(d-lactic acid), ethylene vinyl alcohol (EVOH), ε-caprolactone, ethylvinyl hydroxylated acetate (EVA), polyvinyl alcohol (PVA), polyethylene oxides (PEO), and co-polymers thereof and mixtures thereof, dissolved in chloroform, or acetone, or other suitable solvents. These polymers all have a history of safe and low inflammatory use in the systemic circulation.

A non-polymer coating such as everolimus which has been ionically bound to the metal stent surface can also be used in the present invention.

Using the coating system as described, it has been discovered that it is feasible to coat all of the top, side, and inside surfaces of the stent. By the careful selection of a suitable ratio of solvent to polymer, the viscosity of the solution can be adjusted such that some of the solution will migrate down the sides of the strut and actually inhabit the bottom surface before solidifying, as shown in FIG. 5B. By controlling the dwell time of the delivery tube close to the edge of the stent, the amount of polymer coating the edges or bottom of the stent can be increased or reduced. In the embodiment illustrated in FIG. 3, an underlayer of pure polymer 34 and solvent is applied to the stent surfaces 24 first using the coating system of the invention and the solvent is allowed to evaporate. Then a second layer of polymer 32 is applied containing the bioactive agent.

Figure 8:
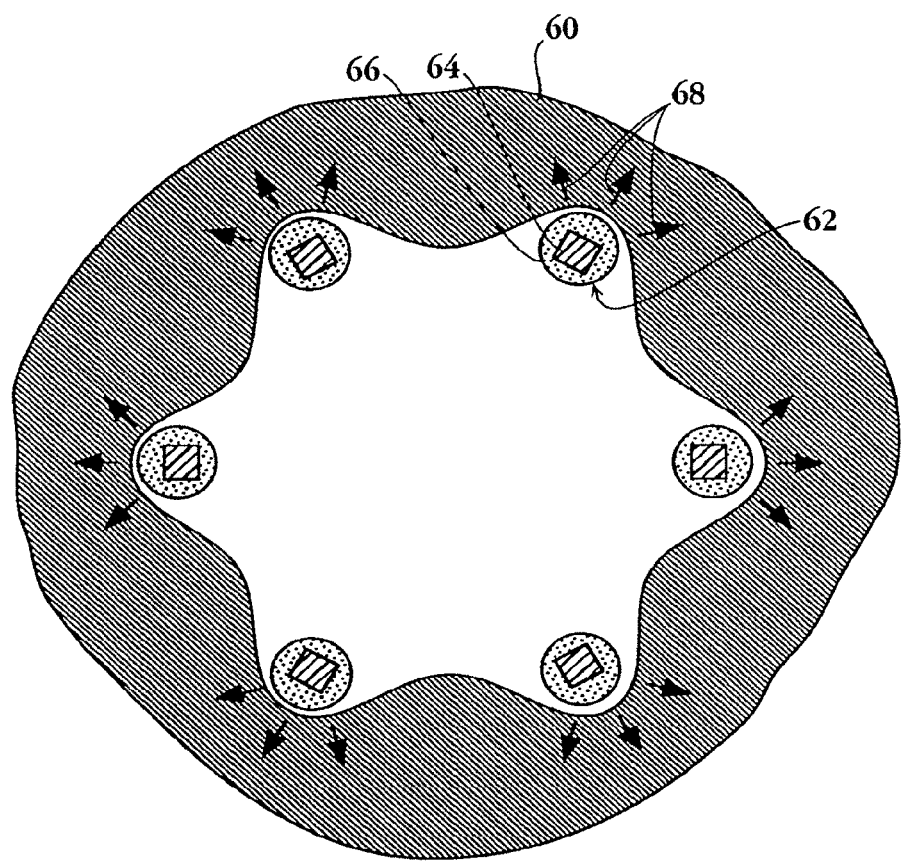
FIG. 8 is a cross-sectional view of a stent in the invention deployed at a vascular site.

As noted above, a secondary agent may be incorporated into the polymer mixture. As an example, heparin in crystalline form may be incorporated into the coating. The heparin crystals are micronized to a particle size of approximately 1-5 microns and added in suspension to the polymer solution. Suitable forms of heparin are those of crystalline form that exhibit bioactivity in mammalian hosts when applied according to the process of the invention, including heparin salts (i.e. sodium heparin and low molecular weight forms of heparin and their salts). Upon deployment of the drug delivering stent into the vessel wall 60, as seen in FIG. 8, the heparin crystals 62 near the surface of the coating of cured polymer 66 begin to dissolve, increasing the porosity of the polymer. As the polymer slowly dissolves, more heparin and bioactive agent are released in a controlled manner, as indicated by 68.

It should be appreciated however, with reference to FIG. 8, that it is not always desirable to coat the inside surfaces of the stent (indicated as 61 in FIG. 8). For example, coating the inside surface of the stent increases the crimped delivery profile of the device, making it less maneuverable in small vessels. And, after implantation, the inside surfaces are directly washed by the flow of blood through the stent, causing any drug released on the inside surface to be lost to the systemic circulation. Therefore, in the embodiments shown in FIGS. 3 and 4, the bulk of the cured polymer and agent is deployed on the outside circumference of the stent supports, and secondarily on the sides. In a preferred embodiment, only a minimum amount of polymer and agent is applied on the inside surfaces of the stent. If desired, it is also possible to have at least a portion of the inside surfaces of the stent uncoated or exposed.

Further, the coating of FIGS. 3 and 4, may be placed onto the stent filament surfaces in a selective manner. The depth of the coated section may correspond to the volume of bioactive coating to be available for presentation to the tissue. It may be advantageous to restrict the coating from certain areas, such as those which could incur high strain levels during stent deployment.

A uniform underlayer may be first placed on the stent surface to promote adhesion of the coating that contains the bioactive agent, and/or to help stabilize the polymer coating on the stent. The primer coat may be applied by using any of the methods as already known in the art, or by the precision dispensing system of the invention. It is also within the scope of the invention to apply a primer coat using a different polymer material, such as parylene (poly(dichloro-para-xylene)), or any other material which exhibits good adhesion to both the base metal substrate and the coating which contains the bioactive agent. Parylene (poly(dichloro-para-xylene)) may be deposited via sputter coating or vapor deposition techniques as is well known in the art (See U.S. Pat. No. 6,299,604). In one embodiment of the present invention, islands or a layer of a coating containing heparin are formed on inside surface(s) of a stent and an anti-proliferation coating containing the drugs of the present invention as described above is formed on outside surface(s) of the stent.

Where it is desired to form a coating with a high drug/polymer substrate ratio, e.g., where the drug constitutes 40-80 weight percent of the coating on a metal stent substrate, it is advantageous to form an underlayer on the stent filaments to stabilize and firmly attach the coating to the substrate. The underlayer may be further processed, prior to deposition of the coating material, by swelling in a suitable solvent, e.g., acetone, chloroform, xylene, or mixtures thereof. This approach is described in Example 5 for preparing a stent having a high ratio of everolimus to poly-dl-lactide.

Here a parylene underlayer is formed on the stent filaments by plasma deposition, and the underlayer then allowed to swell in xylene prior to final deposition of the coating material. The method was effective in producing coating containing 50% drug in one case and 75% drug in another case in a poly-dl-lactide polymer substrate, in a coating having a thickness of only 5-10 microns.

It is also within the scope of the present invention to produce a completely bioerodable stent, as noted above, using the coating system of the current invention. This may be accomplished by making a tubular preform in the shape of the stent to be formed, using an open-top "C-shaped" helical channel into which the dispensing system may deposit the polymer. The preform is open at its outside diameter so that the polymer may be deposited into the preform, typically using one pass, but also multiple passes, if necessary, of the dispensing tube; while creating uniform edges of the stent structure where the polymer is constrained by the preform. The preform is soluble in a solvent which does not dissolve the bio-degradable stent thus created. After the polymer has been deposited and solvent of the polymer solution has evaporated, the assembly may be placed in the solvent which dissolves the preform to free the completed stent structure. A typical material for the preform is sucrose, which may be molded into the desired preform shape using standard injection molding techniques. A typical solvent for the preform is water.

III. Methods of Use and Performance Characteristics

This section describes vascular treatment methods in accordance with the invention, and the performance characteristics of stents constructed in accordance with the invention.

A. Methods The methods of the invention are designed to minimize the risk and/or extent of restenosis in a patient who has received localized vascular injury, or who is at risk of vascular occlusion. Typically the vascular injury is produced during an angiographic procedure to open a partially occluded vessel, such as a coronary or peripheral vascular artery. In the angiographic procedure, a balloon catheter is placed at the occlusion site, and a distal-end balloon is inflated and deflated one or more times to force the occluded vessel open. This vessel expansion, particularly involving surface trauma at the vessel wall where plaque may be dislodged, often produces enough localized injury that the vessel responds over time by cell proliferation and reocclusion. Not surprisingly, the occurrence or severity of restenosis is often related to the extent of vessel stretching involved in the angiographic procedure. Particularly where overstretching is 35% or more, restenosis occurs with high frequency and often with substantial severity, i.e., vascular occlusion.

In practicing the present invention, the stent is placed in its contracted state typically at the distal end of a catheter, either within the catheter lumen, or in a contracted state on a distal end balloon. The distal catheter end is then guided to the injury site, or the site of potential occlusion, and released from the catheter, e.g., by using a trip wire to release the stent into the site, if the stent is self-expanding, or by expanding the stent on a balloon by balloon inflation, until the stent contacts the vessel walls, in effect, implanting the stent into the tissue wall at the site.

Figure 6:
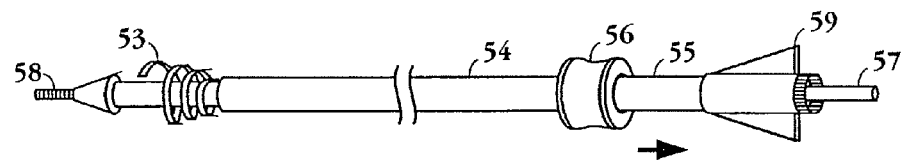
FIG. 6 shows a bioerodable polymer stent constructed in accordance with the present invention, and mounted on a catheter for delivery to a vascular site.

FIG. 6 shows an embodiment of a completely biodegradeable stent of the present invention with a delivery catheter suitable for implantation of the device in a blood vessel of the cardiovascular system, for example a coronary artery, The drawing shows the stent 53, referred to by the inventors as a "Drug Coil", in a partially released position. The stent, which is a self-expanding coil type, is formed from polylactic acid and contains one or more active biological agents of the present invention.

The coil is created using a preform as described, with the final expanded diameter of the preform specified to be slightly larger than the internal lumen size of the vessel to be treated with the coil. After removing the preform, the Drug Coil is wound down by twisting the ends in opposite directions into a coil of smaller radius and thusly compressed along its entire length down under a slideable sheath to a delivery diameter is approximately ⅓ of its final expanded diameter at body temperature. The Drug Coil is thin enough in thickness (approximately 25-125 microns) to be readily bent in a tighter radius to form a compresed coil at the Internal diameter of the sheath. The sheath is slideably disposed on a delivery catheter 55 suitable for delivery of the stent in its compressed state to the target vessel. Sheath 54 has a gripping means 56 at its proximal end by which the angioplasty operator may pull back the sheath and fully release the Drug Coil when the tip of the delivery catheter is in position in the vessel.

The center of the delivery catheter 55 has a lumen of approximately 0.014" diameter, in which a guidewire 57 having a flexible tip 58 may be slideably disposed. The delivery catheter further has a luer hub 59 for connection of the inner lumen to a Y-connector and hemostasis valve, as is well known in the angioplasty art. The OD of the delivery catheter with slideable sheath may be in the range of 2-4 F. (French size), or larger if peripheral arteries are being treated.

Figure 7A:
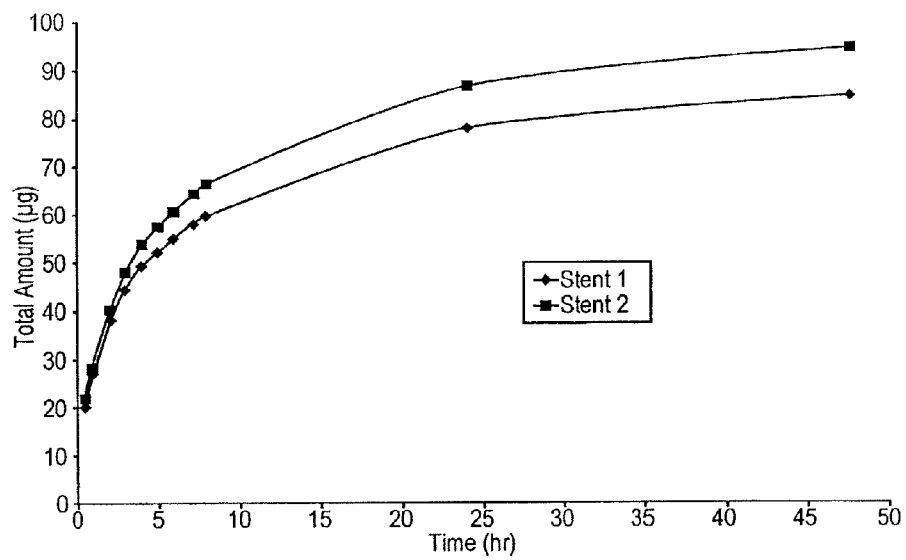
FIGS. 7A and 7B is are plots showing release of everolimus from stents constructed in accordance with the invention.

Since the Drug Coil is fully biodegradeable, it does not affect the patients' chances for later uncomplicated surgery on the vessel, as a full metal jacket does. While bare metal coils are often placed in vessels to create thromboembolism and complete blockage in certain neurovascular applications, surprisingly it has been determined that the biocompatible polymer, poly (dl-Lactic) acid (PDLA), and mixtures thereof, in the disclosed configuration provide adequate mechanical strength to support the injured vessel following angioplasty, and further do not create embolism and thus are exemplary materials for manufacture of Drug Coils of the present invention, Once deployed at the site, the stent begins to release active compound into the cells lining the vascular site, to inhibit cellular proliferation. FIG. 7A shows everolimus release kinetics from two stents constructed in accordance with the invention, each having an approximately 10 micron thick coating (closed squares). Drug-release kinetics were obtained by submerging the stent in a 25% ethanol solution, which greatly accelerates rate of drug release from the stent coating. The graphs indicate the type of drug release kinetics that can be expected in vivo, but over a much longer time scale.

Figure 7B:
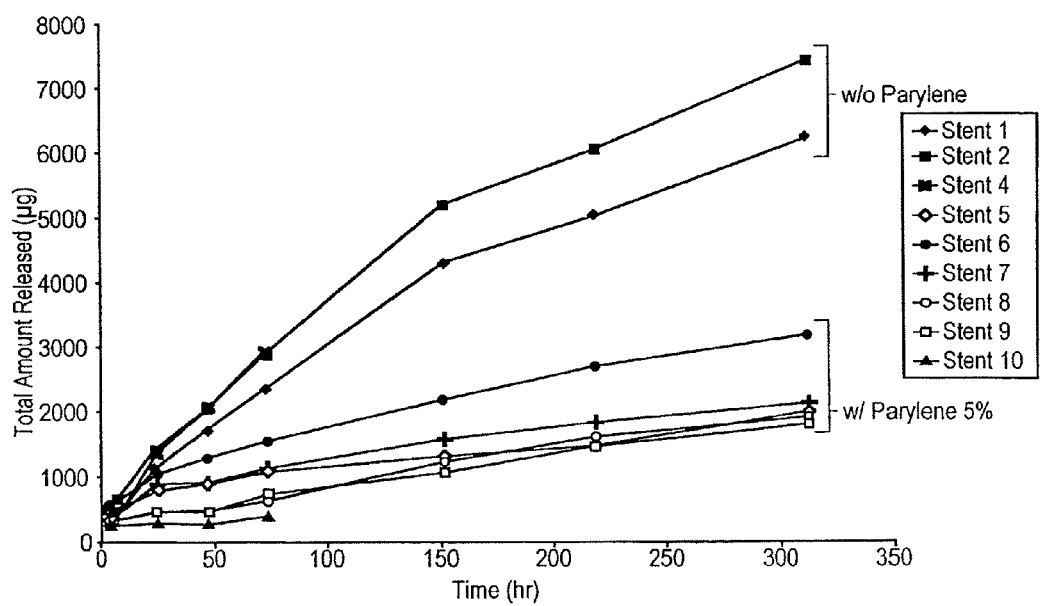

FIG. 7B shows drug release of everolimus from coatings of the present invention on metal stent substrates. The upper set of curves show drug release where the coating has been applied directly to the metal surface. The lower set of curves (showing slower release) were obtained by applying an underlayer or primer coat of parylene to the metal stent surface, followed by coating of the surface with the coating system of the invention. As seen, the primer increases the mechanical adhesion of the coating to the sent surface, resulting in slower breakdown of the bioerodeable coating and slower release of drug. Such a configuaration is useful where it desired to have a strongly attached stent coating which can withstand repeated abrasions during tortuous maneuvering of the drug eluting stent inside the guide catheter and/or vessel, and/or where it is desired to slow down the drug release for extended treatment of the atherosclerosis disease processs at the implant site following implantation of the device. FIG. 8 shows in cross-section, a vascular region 60 having an implanted stent 62 whose coated filaments, such as filament 64 with coating 66, are seen in cross section. The figure illustrates the release of anti-restenosis compound from each filament region into the surrounding vascular wall region. Over time, the smooth muscle cells forming the vascular wall begin to grow into and through the lattice or helical openings in the stent, ultimately forming a continuous inner cell layer that engulfs the stent on both sides. If the stent implantation has been successful, the extent of late vascular occlusion at the site will be less than 50%, that is, the cross-sectional diameter of flow channel remaining inside the vessel will be at least 50% of expanded stent diameter at time of implant.

Trials in a swine restenosis animal model as generally described by Schwartz et al ("Restenosis After Balloon Angioplasty-A Practical Proliferative Model in Porcine Coronary Arteries", Circulation 82: (6):2190-2200, Dec 1990.) demonstrate the ability of the stent of this invention to limit the extent of restenosis, and the advantages of the stent over currently proposed and tested stents, particularly in cases of severe vascular injury, i.e., greater than 35% vessel stretching. The studies are summarized in Example 4.

Briefly, the studies compare the extent of restenosis at 28 days following stent implantation, in bare metal stents, polymer-coated stents, and polymer coated stents containing high or low concentrations of sirolimus (rapamycin) and everolimus.

Table 1 in Example 4 shows that both rapamycin (Rapa-high or Rapa-low) and everolimus stents (C-high or C-low) greatly reduced levels of restenosis, with the smallest amount of restenosis being observed in the high-dose everolimus stent. Similar results were obtained in studies on animals with low injury (Table 2).

Figure 9A:
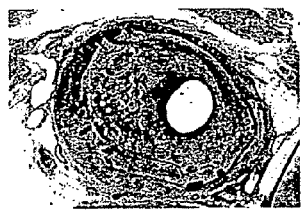
FIGS. 9A-9C are histological sections of a vessel 28 days after implantation of a bare-metal stent.
Figure 10A:
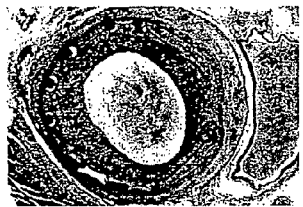
FIGS. 10A-10C are histological sections of a vessel 28 days after implantation of a metal-filament stent with a polymer coating.
Figure 9B:
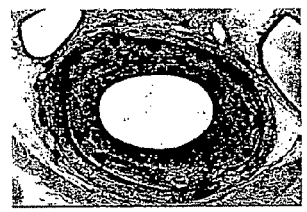
Figure 10B:
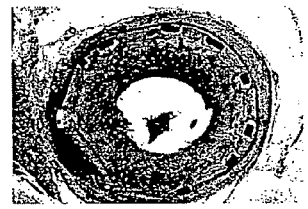
Figure 9C:
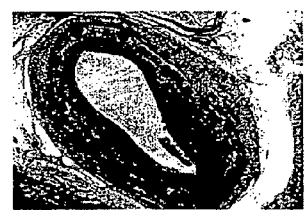
Figure 10C:
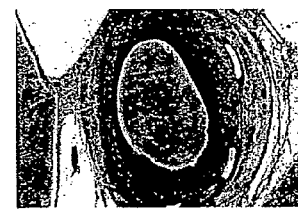
Figure 11A:
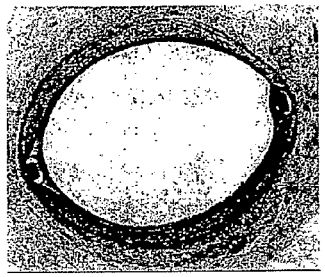
FIGS. 11A-11C and 12A-12C are histological sections of a vessel 28 days after implantation of a metal-filament stent with a polymer coating containing everolimus.
Figure 12A:
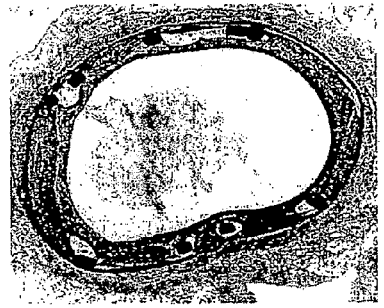
Figure 11B:
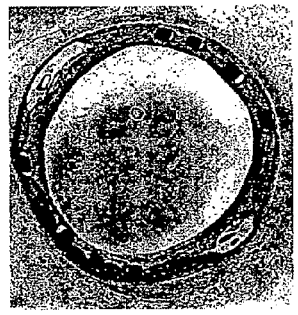
Figure 12B:
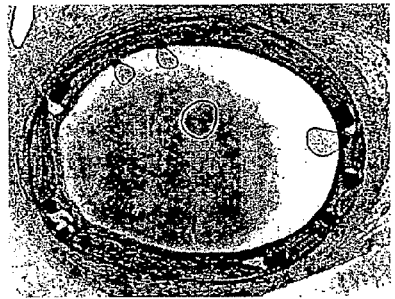
Figure 11C:
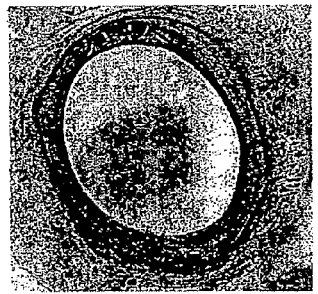
Figure 12C:
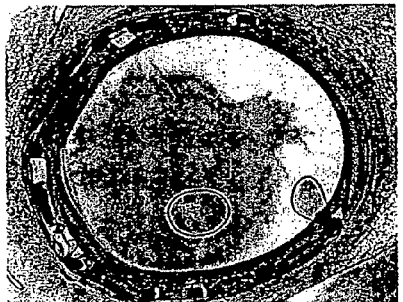
Figure 13:
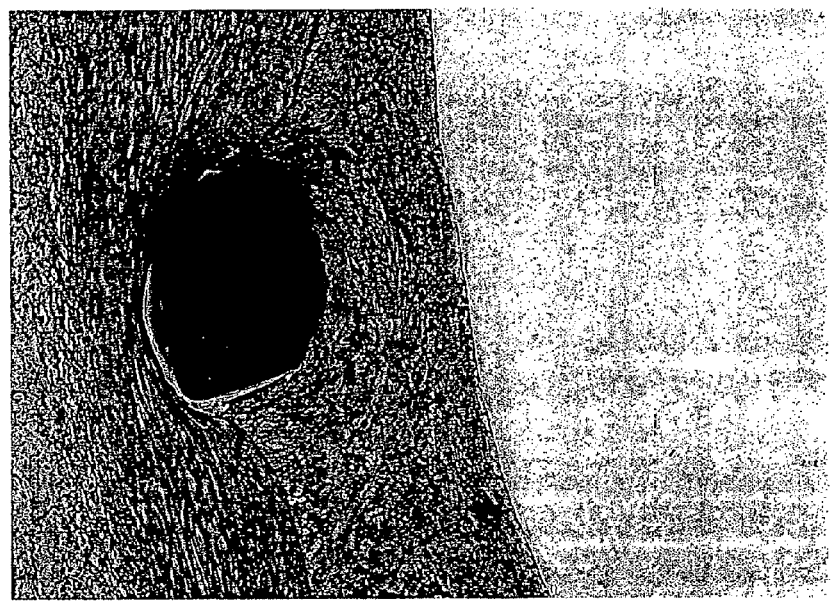
FIG. 13 is an enlarged histological section of a vessel seen with a filament of the stent employed in FIGS. 11A-11C, which been overgrown by new tissue forming a healed vessel wall.

FIGS. 9A-9C are examples of stent cross-sections of neointimal formation at 28 days in a bare metal S-Stent (available from Biosensors International Inc, Newport Beach, Calif.). FIGS. 10A-10C are examples of neointimal formation in a polymer-coated (no drug) S-Stent; and FIGS. 11A-11C and 12A-12C of neointimal formation in everolimus/polymer coated stents. In general, the vessels with everolimus-coated stent treatment appeared to be well-healed with a well established endothelial layer, evidence of complete healing and vessel homeostasis at 28 days. FIG. 13 is an example of vessel cross-section at 91 X magnification showing healing and establishment of an endothelial layer on the inside of the vessel lumen at 28 days post implant. The photographs indicate that the most favorable combination for elimination of restenosis at 28 days is the C-high, or C-Ulight formulation (see Example 4), which contained 325 microgram and 275 microgram dosage of everolimus on a 18.7 mm length stent. The data predicts a 50% reduction in restenosis compared to a currently marketed bare metal stent (the S-Stent) at 28 days followup in outbred juvenile swine. The data also shows that the drug everolimus is better than, or at least equivalent to the 180 microgram dosage of sirolimus on the same stent/polymer delivery platform. These results are supported by morphometric analysis (Example 4).

Figure 15:
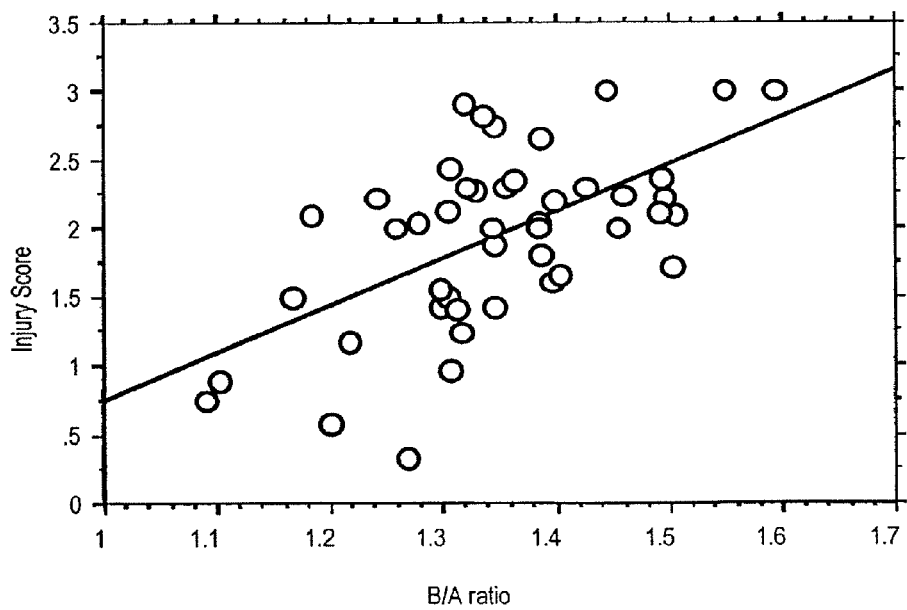
FIG. 15 shows a correlation plot between injury score (Y axis) and B/A (balloon/artery) ratio at time of stent implantation.

FIG. 15 shows the relationship between balloon overstretch of the vessel, as measured by balloon/artery ration (B/A Ratio), and vessel injury in the animal experiment. This data shows that use of an over-expanded angioplasty balloon to create a high controlled vessel injury is a reasonably accurate method of creating a predictable and known vascular injury in the porcine model.

Figure 14:
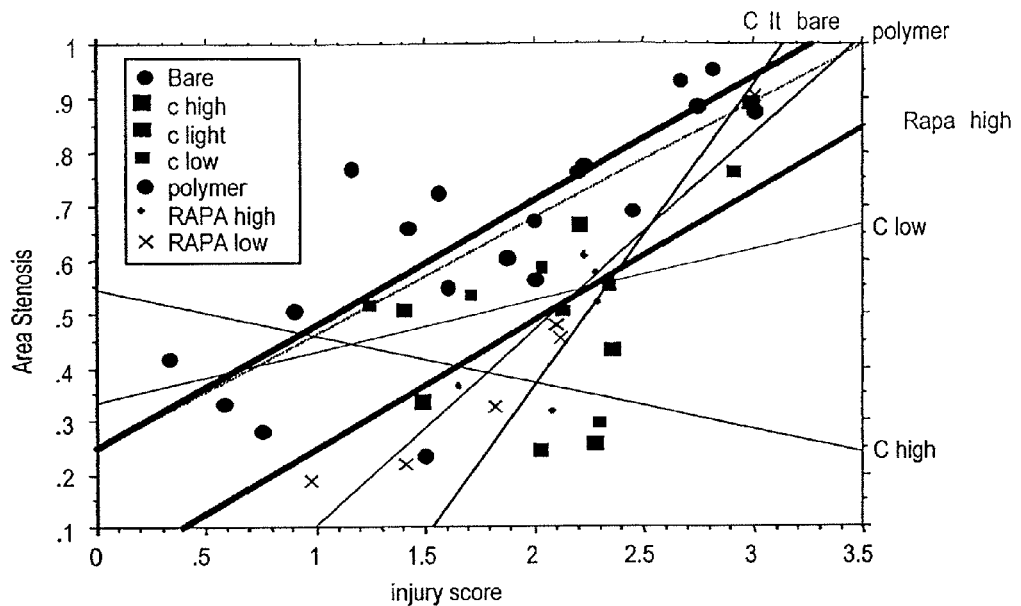
FIG. 14 is a plot of area of stenosis at 28 days post-implant, as a function of injury score, with a variety of different stents, including those constructed in accordance with the invention.

FIG. 14 are "best fit" linear regression curves of the chosen dosings of agents in polymers, coated on the S-Stent, relating injury score to area stenosis at follow-up. Area Stenosis is an accurate indicator of neointimal formation which is determined by morphometric analysis. As can be seen from this chart, the high everolimus stent was the only coating in the group of samples tested that exhibited a negative slope vs. increasing injury score. This analysis suggests that the C-high coating may be capable of controlling restenosis in an injured coronary artery which is virtually independent of injury score. None of the other coating formulations tried exhibited this unique characteristic.

From the foregoing, it can be seen how various objects and features of the invention are met. In one aspect, the invention provides a bioerodable stent coating with high drug/polymer ratios, e.g., 40-80% drug by weight. This feature allows continuous delivery of an anti-restenosis compound over an extended period from a low-profile stent. At the same time, the total amount of polymer breakdown components such as lactide and lactic acid released during bioerosion is relatively small, minimizing possible side effects, such as irritation, that may result from bioerosion of the stent coating.

In another aspect, the invention provides an improved method for treating or inhibiting restenosis. The method, which involves a novel combination of macrocyclic triene immunosuppressant compound in a stent polymer coating, provides at least the effectiveness against restenosis as the best stent in the prior art, but with the added advantage over the prior art that the efficacy of the method appears to be independent of the extent of injury, and the method may offer a greater degree of endothelialization of the stented vessel.

Finally, the method provides a completely bioerodable stent that has the advantageous features just mentioned and the more design flexibility than a metal-body stent, particularly in total stent length and future operability on the treated vessel.

The following examples illustrate various aspects of the making and using the stent invention herein. They are not intended to limit the scope of the invention.

Example 1

Preparation of Everolimus and Derivatives thereof

STEP A. Synthesis of 2-(t-butyldimethylsilyl)oxyethanol (TBS glycol).

154 ml of dry THF and 1.88 g NaH are stirred under in a nitrogen atmosphere in a 500 ml round bottom flask condenser. 4.4 mL dry ethylene glycol are added into the flask, resulting in a large precipitate after 45 minutes of stirring. 11.8 g tert-butyldimethylsilyl chloride is added to the flask and vigorous stirring is continued for 45 minutes. The resulting mixture is poured into 950 mL ethylether. The ether is washed with 420 mL brine and solution is dried with sodium sulfate. The product is concentrated by evaporation of the ether in vacuo and purified by flash chromatography using a 27×5.75 cm column charged with silica gel using a hexanes/$Et_2O$ (75:25v/v) solvent system. The product is stored at 0° C.

STEP B. Synthesis of 2-(t-butyldimethylsilyl)oxyethyl triflate (TBS glycol Trif).

4.22 g TBS glycol and 5.2 g 2,6-lutidine are combined in a double-necked 100mL flask with condenser under nitrogen with vigorous stirring. 10.74 g of trifluoromethane sulfonic anhydride is added slowly to the flask over a period of 35-45 minutes to yield a yellowish-brown solution. The reaction is then quenched by adding 1 mL of brine, and the solution washed 5 times in 100 mL brine to a final pH value of between 6-7. The solution is dried using sodium sulfate, and concentrated by evaporation of the methylene chloride in vacuo. The product is purified using a flash chromatography column of approximately 24×3 cm packed with silica gel using hexane/$Et_2O$ (85:15v/v) solvent system, then stored at 0° C.

STEP C. Synthesis of 40-0-[2-(t-butyldimethylsilyl)oxy]ethyl-rapamycin (TBS Rap).

400 mg rapamycin, 10 mL of toluene, and 1.9 ml 2,6-lutidine are combined and stirred in a 50 mL flask maintained at 55-57deg C. In a separate 3 mL septum vial, 940 µl 2,6-lutidine is added to 1 mL toluene, followed by addition of 2.47 g TBS glycol Trif. The contents of the vial are added to the 50 mL flask and the reaction allowed to proceed for 1.5 hours with stirring. 480 µ2,6-lutidine plus an additional 1.236 g TBS glycol Trif is added to the reaction flask. Stirring is continued for an additional hour. Finally, a second portion of 480 µl 2,6-lutidine and 1.236 g TBS glycol Trif is added to the mixture, and the mixture is allowed for an additional 1-1.5 hours. The resulting brown solution is poured through a porous glass filter-using vacuum. The crystal like precipitate is washed with toluene until all color has been removed. The filtrate is then washed with 60 mL saturated $NaHCO_3$ solution twice and then washed again with brine. The resulting solution is dried with sodium sulfate and concentrated in vacuo. A small quantity of a hexane/EtOAc (40:60 v/v) solvent is used to dissolve the product, and purification is achieved using a 33×2 cm flash chromatography column packed with silica gel, and devloped with the same solvent. The solvent is removed in vacuo and the product stored at 5° C.

STEP D. Synthesis process of 40-0-(2-hydroxyl)ethyllapamycin (everolimus).

A pyrex glass dish (150×75 mm) is filled with ice and placed on a stirring plate. A small amount of water is added to provide an ice slurry. 60-65 mg of TBS-Rap is first dissolved in a glas vial by adding 8 ml methanol. 0.8 ml 1N HCl is added to the vial, the solution is stirred for 45 minutes and then neutralized by adding 3 mL aqueous saturated $NaHCO_3$. 5 mL brine is added to the solution, followed with 20 mL EtoAc, resulting in the formation of two phases. After mixing of the phases, a separatory funnel is used to draw off the aqueous layer. The remaining solvent is washed with brine to a final pH of 6-7, and dried with sodium sulfate. The sodium sulfate is removed using a porous glass filter, and the solvent removed in vacuo. The resulting concentrate is dissolved in EtoAc/methanol (97:3) and then purified using in a 23×2 cm flash chromatography column packed with silica gel, and developed using the same solvent system. The solvent is removed in-vacuo and the product stored at 5° C.

Example 2

Preparation of Stent Containing Everolimus in a Poly-d/-lactide Coating 100 mg poly (dl-lactide) was dissolved into 2 mL acetone at room temperature. 5 mg everolimus was placed in a vial and 400 µL lactide solution added. A microprocessor-controlled syringe pump was used to precision dispense 10 µL of the drug containing lactide solution to the stent strut top surfaces. Evaporation of the solvent resulted in a uniform, drug containing single polymer layer on the stent.

A 15 µL volume was used in a similar manner to coat the stent top and side strut surfaces, resulting in a single layer coating on the stent strut top and sides.

Example 3

In vitro drug release from stent containing everolimus in a poly-dl-lactide coating In vitro drug release was conducted by placing the coated stents into 2 mL pH 7.4 phosphate buffered saline solution containing 25% ETOH, and preserved with 0.05% (w/v) sodium azide and maintained at 37 ° C. Sampling was periodically conducted by withdrawing the total buffer volume for drug measurement while replacing solution with a similar volume of fresh buffer (infinite sink). FIG. 7 illustrates drug release from two similar stents coated with a single polymer layer microdispensed in this manner.

Example 4

Animal Implant Tests

A. QCA Results of safety and dose-finding studies in swine
Rationale:

It was reasoned that the most challenging treatment condition for the drug eluting stent is a severely injured vessel, as it is known that the degree of restenosis (neointimal formation) increases directly with extent of vessel injury. Experiments were conducted in pigs, and a substantial number of the vessels which were the target of drug-coated stent implants were seriously injured (averaging approximately 36% overstretch injury of the vessel) using an angioplasty balloon. This caused severe tearing and stretching of the vessel's intimal and medial layers, resulting in exuberant restenosis at 28 days post implant. In this way, it was possible to assess the relative effectiveness of various dosings of drug, and drug to polymer weight ratios on the same metal stent/polymer platform for reduction of restenosis at 28 days post-implant.

Definitions:
1. Bare stent: An 18.7 mm bare metal stent of a corrugated ring design (i.e. a currently marketed "S-Stent" as manufactured by Biosensors Intl., Inc).
2. C-high: An 18.7 mm long stent carrying 325 micrograms of everolimus in a PDLA (poly-dl-lactate) polymer coating.
3. C-low: An 18.7 mm long stent carrying 180 micrograms of everolimus in a PDLA polymer coating.
4. Rap-high: An 18.7 mm long stent carrying 325 micrograms of sirolimus in a PLA polymer coating.
5. Rap-low: An 18.7 mm long stent carrying 180 micrograms of sirolimus in a PDLA polymer coating.
6. C-Ulight: An 18.7 mm long stent carrying 275 micrograms of everolimus in an ultrathin coating of PDLA polymer (37%drug to polymer weight ratio)
7, C-Ulow: An 18.7 mm long stent carrying 180 micrograms of everolimus or equivalent in an ultrathin coating of PDLA polymer (37% drug to polymer weight ratio)
8. Polymer stent: An 18.7 mm S-Stent stent covered by PDLA polymer coating only.
9. B/A is the final inflated balloon-to-artery ratio, an indication of the extent of overstretching of the vessel.
10. Mean Lumen Loss (MLL)-Average of 3 measurements taken inside the stent internal lumen at time of implant minus average of 3 measurements at follow-up angiography indicates the amount of neointima that has formed inside the stent.

Methods:

Drug-eluting stents using a metal wire-mesh scaffold of a corrugated ring design (i.e. S-Stent) and polymer coating were implanted in out-bred juvenile swine (alternately Yucatan Minipigs for implant studies lasting longer than 28 days), using different dosings of either the drug everolimus or the drug sirolimus. At time of implant, Quantitative Coronary Angiography (QCA) was performed to measure the diameter of the vessels both before and after stent implantation. At 28 days, or longer when specified in the table below, the animals were again subjected to QCA in the area of the stent, prior to euthanization.

Following euthanasia of animals according to approved protocols, the hearts were removed from the animals and pressurized formaldehyde solution was infused into the coronary arteries. The coronary segments containing the stents were then surgically removed from the surface of the heart and subsequently fixed in acrylic plastic blocks for transverse sectioning with a diamond saw. 50 micron thick sections of the acrylic material containing cross-sections of the vessels located proximally, center, and distally were then optically polished and mounted to microscope slides.

A microscope containing a digital camera was used to generate high resolution images of the vessel cross-sections which had been mounted to slides. The images were subjected to histomorphometric analysis by the procedure as follows:

A computerized imaging system Image Pro Plus 4.0 through an A.G. Heinze slide microscope for a PC-based system was used for histomorphometric measurements of:
1. The mean cross sectional area and lumen thickness (area circumscribed by the intima/neointimal-luminal border); neointimal (area between the lumen and the internal elastic lamina, IEL, and when the IEL was missing, the area between the lumen and the remnants of media or the external elastic lamina, EEL); media (area between the IEL and EEL); vessel size (area circumscribed by the EEL but excluding the adventitial area); and adventitia area (area between the periadventitial tissues, adipose tissue and myocardium, and EEL).
2. The injury score. To quantify the degree of vascular injury, a score based on the amount and length of tear of the different wall structures was used.

The degree of injury was calculated as follows:
0=intactIEL
1=ruptured IEL with exposure to superficial medial layers (minor injury)
2=ruptured IEL with exposure to deeper medial layers (medial dissection)
3=ruptured EEL with exposure to the adventitia.

The following table shows the results of the QCA analysis (measurements of mean late loss due to restenosis) at follow-up QCA. The data in the tables below under column heading "Neo-intimal area" report the results of morphometric analysis of stents and vessels removed from the pigs at follow-up (f/u):

TABLE 1

Results of "high injury" experiment

| Device Description | B/A Ratio (avg) | Days f/u | Mean Lumen Loss, mm (avg) | Neo-Intima Area (mm$^2$) | Stent numbers |
|---|---|---|---|---|---|
| Bare Metal Stent | 1.33 | 28 | 1.69 | 5.89 | 31, 39, 40, 45, 47, 50 |
| Polymer Coated | 1.36 | 28 | 2.10 | 5.82 | 32, 41, 43, 48, 51, 60 |
| Rapa-high | 1.39 | 28 | 1.07 | 3.75 | 42, 44, 49, 65, 69, 73 |
| Rapa-low | 1.42 | 28 | 0.99 | 2.80 | 52, 56, 61, 64, 68, 72 |
| C-high | 1.37 | 28 | 0.84 | 3.54 | 54, 55, 59, 63 |
| C-low | 1.36 | 28 | 1.54 | 3.41 | 53, 57, 58, 62, 66, 70, 74 |
| C-Uhigh | 1.36 | 28 | 0.85 | 2.97 | 67, 75, 92, 103 |

B. Low-injury studies

To further determine which dosage of everolimus would be best in a lightly injured vessel, more typical of the patient with uncomplicated coronary disease and a single denovo lesion, the everolimus eluting stents were implanted to create moderate to low overstretch injury (approximately 15%). Farm swine were used for a 30 day experiment, and adult Yucatan minipigs were implanted for a 3 month safety study. The angiographic results were as follows:

TABLE 2

QCA Results of "low injury" experiments

| Device Description | B/A ratio | Days post implant | Mean Lumen Loss | Neo-Intima Area (mm$^2$) | Stent numbers |
|---|---|---|---|---|---|
| Bare Metal Stent | 1.14 | 28 | 0.95 | 2.89 | 20, 22, 26, 29 |
| Bare Metal Stent | 1.13 | 90 | | | 76, 80, 84, 87, 91 |
| C-Uhigh | 1.15 | 28 | 0.60 | 2.14 | 94, 96, 98, 102 |
| C-Ulow | 1.09 | 28 | 0.49 | 2.26 | 93, 95, 97, 100, 101 |
| C-Uhigh | 1.15 | 90 | | | 77, 81, 85, 86, 90 |

The above data predict that with either the C-Ulow or C-Uhigh doses of everolimus will produce a 45-48% reduction in neointimal formation in a low to moderately injured vessel.

C. Morphometric analysis

The total cross-sectional area inside each stent, and cross-sectional area of new tissue (neo-intima) that had formed inside the stent were measured by computer, and the %Area stenosis computed. The average vessel injury score, neo-intimal area, and %area stenosis for each formulation of drug and polymer, averaging 3 slices per stent, is shown in the table below.

TABLE 3

Results of "high injury" experiment

| Device Description | Injury Score | Days f/u | Neo-Intimal Area (mm$^2$) | % Area Stenosis | Stent numbers |
|---|---|---|---|---|---|
| Bare Metal Stent | 1.9 | 28 | 5.89 | 0.72 | 31, 39, 40, 45, 47, 50 |
| Polymer Coated | 2.11 | 28 | 5.82 | 0.70 | 32, 41, 43, 48, 51, 60 |
| Rapa-high | 2.10 | 28 | 3.75 | 0.55 | 42, 44, 49, 65, 69, 73 |

TABLE 3-continued

Results of "high injury" experiment

| Device Description | Injury Score | Days f/u | Neo-Intimal Area (mm$^2$) | % Area Stenosis | Stent numbers |
|---|---|---|---|---|---|
| Rapa-low | 1.90 | 28 | 2.80 | 0.43 | 52, 56, 61, 64, 68, 72 |
| C-high | 1.89 | 28 | 3.54 | 0.38 | 54, 55, 59, 63 |
| C-low | 2.1 | 28 | 3.41 | 0.53 | 53, 57, 58, 62, 66, 70, 74 |
| C-Uhigh | 2.13 | 28 | 2.97 | 0.45 | 67, 75, 92, 103 |

Discussion: Morphometric analysis is considered a highly accurate method of measuring in-stent restenosis in the pig coronary model. In the high injury model, the C-High formulation produced the lowest amounts of neointima formation in the High Injury Experiment at 28 days, however, the C-Uhigh had the highest injury score of the group, and still managed a very low % Area Stenosis of 0.45. Therefore, the data independently confirm the findings of the QCA analysis, and supports the choice of C-Uhigh as the preferred formulation for human trials.

D. Histological analysis

The slides for the C-Uhigh and Sirolimus Low were submitted to an experienced cardiac pathologist, who reviewed the vessel cross-sections for evidence of inflammation, fibrin, and endothelialization of the newly healed vessel lumen. No difference was found between the histological changes caused by the sirolimus and everolimus eluting stents. In general, the vessels appeared to be well-healed with a well established endothelial layer, evidence of complete healing and vessel homeostasis at 28 days. FIG. 13 is an example of vessel cross-section at 91X magnification showing healing and establishment of an endothelial layer on the inside of the vessel lumen at 28 days post-implant.

E. Comparison to published results

Carter et.al. have published results of sirolimus-coated stents using the Palmaz Schatz metal stent in swine. A table comparing the published results of Carter to Biosensors' experimental results is shown below:

TABLE 4

| DEVICE DESCRIPTION | Vessel Overstretch % | Mean Late Loss (mm) mm | Std Deviation (mm) mm | Neointima Cross-Sectional Area (mm$^2$) mm$^2$ |
|---|---|---|---|---|
| S-Stent BARE METAL control | 33.5% +− 9.2% | 1.80 | +−0.5 | 7.6 |
| S-Stent Polymer-only Coated | 34.9% +− 4.8% | 2.02 | +−0.8 | 8.5 |
| S-Stent Polymer/Rapamycin 325 microGrams | 32.9% +− 10.1% | 0.66 | +−0.2 | 3.27 (−57% vs control) |
| S-Stent Polymer/Drug #1 325 microGrams | 36.8% +− 8.5% | 0.74 | +−0.3 | 3.61 (−50% vs control) |
| PS Stent BARE* control | 10-20% | 1.19 | — | 4.5 |
| PS Stent Polymer-only | 10-20% | 1.38 | — | 5.0 |
| PS Rapamycin-eluting stent* 166 microGrams | 10-20% | 0.70 | — | 2.9 (−35.5% vs control) |
| PS Rapamycin-eluting Stent* 166 microGrams | 10-20% | 0.67 | — | 2.8 (−37.7% vs control) |

TABLE 4-continued

| DEVICE DESCRIPTION | Vessel Overstretch % | Mean Late Loss (mm) mm | Std Deviation (mm) mm | Neointima Cross-Sectional Area (mm²) mm² |
|---|---|---|---|---|
| (Slow Release) PS Rapamycin-eluting Stent* 450 microGrams | 10-20% | 0.75 | — | 3.1 (−31.1% vs control) |

Example 5

Preparation of Stent with High Drug Loading

As-marketed metal corrugated-ring stents ("S-stent, corrugated ring design, Biosensors Intl), 14.6 mm in length, were coated with an approximately 2 micron thick layer of parylene 'C' primer coating using a plasma deposition process.

Parylene coated stents were placed in xylene overnight at ambient temperature. A stock poly(D,L)-lactic acid solution containing 50 ug/uL polylactic acid (PLA) was prepared by dissolving 100 mg PLA in 2 mL acetone.

To prepare stents containing a drug to polymer ratio of 50%, 5 mg everolimus was dissolved in 100 µL of the PDLA stock solution. An additional 20 µL acetone was added to aid in dispensing the solution. The stents were removed from the xylene and carefully blotted to remove solvent. A total of 5.1 µL coating solution was dispensed onto the outer surface of each stent. The stents were dried at ambient temperature and placed into overnight desiccation. This resulted in a total of 212 µg everolimus contained in 212 µg PLA per stent.

To prepare stents containing a drug to polymer ratio of 75%, 5 mg everolimus and 33.3 µL stock PLA solution were mixed. An additional 33.3 µL acetone was added and the mixture was dissolved. Stents were removed from the xylene and blotted similar to above. A total of 2.8 µL coating solution was dispensed onto the outer surface of each stent. The stents were dried at ambient temperature and placed into overnight desiccation. This resulted in a total of 212 µg everolimus contained in 70 µg PLA per stent.

The finished stents exhibited an approximately 5 microns-thick coating of everolimus/PDLA, or slightly milky appearance, which was smoothly distributed on the top and side surfaces, and firmly attached to the metal strut surfaces.

It is claimed:

1. An endovascular stent for placement at a vascular injury site, for inhibiting restenosis at the site, comprising a body having an open-lattice structure formed of linked filaments said filaments having outside, side and inside surfaces, and carried on the one or more filaments a drug-release coating having a thickness of between 3-30 microns, wherein the coating is applied as a fluid to the outside surfaces but not on the inside surfaces of said filaments, wherein the inside surfaces are free of any coatings; and the coating is composed of (i) a poly-lactide polymer substrate and (ii) a macrocyclic triene compound having the form:

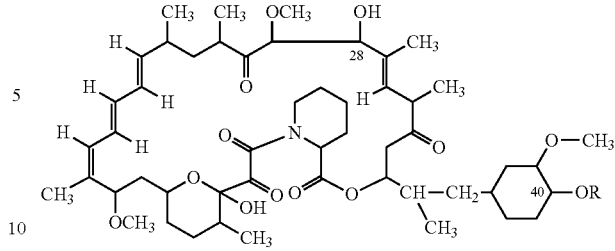

where R is $CH_2$—$CH_2$—OH or H, said stent being expandable from a contracted condition in which the stent can be delivered to a vascular injury site via catheter, and an expanded condition in which the stent coating can be placed in contact with the vessel at the injury site, said coating being effective to release an amount of the compound to inhibit restenosis at the site.

2. The stent of claim 1, wherein the filaments are poly-l-lactide, and the polymer substrate in the coating is selected from the group consisting of poly-l-lactide or poly-dl-lactide.

3. The stent of claim 1 wherein the drug-release coating of poly-lactide polymer is a co-polymer.

4. The stent of claim 3 wherein the co-polymer is comprises poly-lactide and ε-caprolactone.

5. The stent of claim 1, wherein the polymer substrate in the coating is formed of poly-dl-lactide having a thickness between 3-20 microns.

6. The stent of claim 3, which further includes a parylene polymer undercoat having a thickness of between 1-3 microns, disposed between the filaments of the stent body and said poly-lactide coating.

7. The stent of claim 3, wherein said coating includes the compound at an initial concentration of between 50 and 75 weight percent of coating.

8. The stent of claim 1, further comprising a polymer undercoat disposed between the filaments of the stent body and said drug-release coating.

9. The stent of claim 8, wherein said polymer undercoat is formed of a polymer selected from the group consisting of ethylene vinyl alcohol, parylast, silicone, a fluoropolymer, and parylene.

10. The stent of claim 1, wherein said coating further includes a bioactive agent selected from the group consisting of antiplatelet agents, fibrinolytic agents, and thrombolytic agents.

11. The stent of claim 1, wherein the polymer substrate in the coating is formed of poly-dl-lactide.

12. The stent of claim 1 wherein R is H.

13. The stent of claim 1 wherein the filaments are metal.

14. The stent of claim 1 wherein the filaments are bioerodible.

15. The stent of claim 1 wherein the coating is on the outside surfaces and side surfaces of said filaments.

16. The stent of claim 1 wherein the drug release coating is composed of (i) 25-55 weight percent polymer substrate and (ii) 45-75 weight percent macrocyclic triene compound.

17. The stent of claim 1 wherein the drug release coating is composed of (i) 20-70 weight percent poly-lactide polymer substrate and (ii) 30-80 weight percent macrocyclic triene.

* * * * *